United States Patent [19]

Bossert et al.

[11] 4,177,278
[45] Dec. 4, 1979

[54] 2-ALKYLENEAMINODIHYDROPYRIDINES COMPOUNDS, THEIR PRODUCTION AND THEIR MEDICINAL USE

[75] Inventors: Friedrich Bossert, Wuppertal; Egbert Wehinger, Velbert; Arend Heise, Wuppertal; Stanislav Kazda, Wuppertal; Kurt Stoepel, Wuppertal; Robertson Towart, Wuppertal; Wulf Vater, Leverkusen; Klaus Schlossmann, Wuppertal, all of Fed. Rep. of Germany

[73] Assignee: Bayer Aktiengesellschaft, Leverkusen, Fed. Rep. of Germany

[21] Appl. No.: 886,971

[22] Filed: Mar. 15, 1978

[30] Foreign Application Priority Data

Apr. 5, 1977 [DE] Fed. Rep. of Germany ....... 2715182
Sep. 6, 1977 [DE] Fed. Rep. of Germany ....... 2740080

[51] Int. Cl.² .................... C07D 213/55; A61K 31/44
[52] U.S. Cl. .................................. 424/266; 542/455; 546/257; 546/258; 546/284; 546/321
[58] Field of Search ................ 260/294.8 F, 294.8 G, 260/295.5 R, 294.9, 295.5 B, 294.8 C; 542/455; 546/321

[56] References Cited

U.S. PATENT DOCUMENTS 3,867,393  2/1975  Meyer et al. .................... 546/321

Primary Examiner—Alan L. Rotman
Attorney, Agent, or Firm—Sprung, Felfe, Horn, Lynch & Kramer

[57] ABSTRACT

The invention includes the provision of 2-alkyleneaminodihydropyridines and salts thereof and are useful, inter alia, as coronary dilators and antihypertensive agents. Also included in the invention are pharmaceutical compositions containing said 2-alkyleneaminodihydropyridines and methods of treatment involving the use of said compounds or compositions.

17 Claims, No Drawings

2-ALKYLENEAMINODIHYDROPYRIDINES COMPOUNDS, THEIR PRODUCTION AND THEIR MEDICINAL USE

The present invention relates to certain new 2-alkyleneaminodihydropyridines, a process for their production and to their use as medicaments, in particular as agents having an influence on the circulation.

It has already been disclosed that 2,6-dimethyl-4-phenyl-1, 4-dihydropyridine-3,5-dicarboxylic acid diethyl ester is obtained when benzylideneacetoacetic acid ethyl ester is reacted with β-amino-crotonic acid ethyl ester or acetoacetic acid ethyl ester and ammonia (Knoevenagel, Ber. dtsch. chem. Ges. 31, 743 (1898)). Furthermore, it is known that certain 1,4-dihydropyridines have interesting pharmacological properties (F. Bossert, W. Vater, Naturwissenschaften 58, 578 (1971)).

The present invention provides compounds which are 2-alkyleneaminodihydropyridines of the following general formula or salts thereof

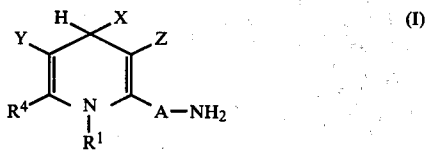

in which $R^1$ is hydrogen, alkyl, alkoxyalkyl or aralkyl, wherein, preferably, each alkyl group contains up to 12 carbon atoms, each aryl moiety is mono- or bi-cyclic carbocyclic aryl and wherein each of the alkyl group and moieties and the aryl moiety is optionally substituted, A is a straight-chain or branched divalent alkylene radical, preferably having up to 6 carbon atoms Y and Z are the same or different and each is (a) a group $COOR^2$ or $COR^2$, wherein $R^2$ is alkyl, alkenyl, alkinyl, alkoxyalkyl, hydroxyalkyl, aminoalkyl, alkylaminoalkyl, alkylaminoaralkyl or aralkyl, wherein, preferably, each alkyl, alkenyl or alkinyl group contains up to 12 carbon atoms and each aryl moiety is mono- or bi-cyclic carbocyclic aryl and wherein each of the alkyl group and moieties and the aryl moiety is optionally substituted;

(b) a cyano radical; or (c) a radical $SO_{(n)}—R^3$, wherein $R^3$ is alkyl, alkenyl, alkoxyalkyl, aminoalkyl, alkylaminoalkyl, aryl or aralkyl, wherein, preferably, each alkyl or alkenyl group contains up to 12 carbon atoms and each of the alkyl and aryl groups and moieties is optionally substituted, and n is an integer having a value of 0, 1 or 2, $R^4$ is hydrogen, or alkyl, preferably contain up to 12 carbon atoms, optionally substituted by alkoxy, preferably, containing up to 12 carbon atoms, or another substituent, or is a radical $A—NH_2$, wherein A has the same meaning as defined hereinbefore, and X is aryl, preferably, mono- or bi-cyclic carbocyclic aryl, optionally substituted by from one to three identical or different substituents each of which is phenyl, alkyl, alkenyl, alkinyl, alkoxy, alkinoxy, acyloxy, halogen, trifluoromethyl, trifluoromethoxy, hydroxyl, nitro, cyano, azido, amino, alkylamino, acylamino, carbalkoxy, carboxamido, sulphonamido or $SO_n$-alkyl wherein n has the same meaning as before, or a quinolyl, pyridyl, pyrimidyl, thienyl, furyl or pyrryl radical which is optionally substituted by alkyl, alkylamino, nitro or halogen, or an optionally substituted aralkyl, cycloalkyl, cycloalkenyl or styryl radical, preferably, each of the alkyl, alkenyl or alkinyl group contains up to 12 carbon atoms, each aryl group is, preferably mono- or bi-cyclic carbocyclic aryl and each cycloalkyl or cycloalkenyl group preferably contains 3 to 8, more preferably 5 to 6 carbon atoms.

Among the new salts of the invention those salts that are pharmaceutically acceptable are particularly important and are preferred.

In a further aspect the present invention provides a process for the production of a compound of the invention in which a 2-alkylenephthalimido-1,4-dihydropyridine of the formula II

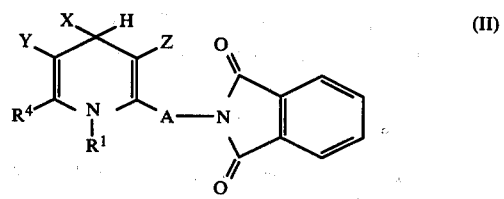

in which $R^1$, A, X, Y and Z have the same meaning as defined hereinbefore in formula (I) and $R^4$ has the same meaning as defined hereinbefore or is a radical or the formula

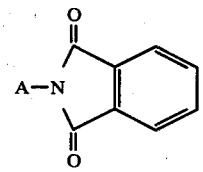

wherein A has the same meaning as defined hereinbefore is subjected to hydrolysis or hydrazinolysis with the splitting off of a phthalic acid group(s) so as to produce the compound of formula (I), optionally in the presence of an inert organic solvent.

By reacting a free amine compound of the formula (I) thus obtained with a suitable organic or inorganic acid by methods which are in themselves known, acid addition salts, particularly the pharmaceutically acceptable acid addition salts, which can also be used according to the invention, are conveniently obtained.

The compounds of the invention exhibit powerful pharmacological actions. In particular, they have valuable actions on the circulatory system in warm-blooded animals and can preferably be used as coronary agents, antihypertensive agents and agents for increasing the peripheral blood circulation. Because of their novel structure, in particular because of the superior solubility of the compounds according to the invention resulting from the presence of the amino group, and because of their various modes of action, the use of the compounds according to the invention represents an enrichment of pharmacy.

The phthalimido 1,4-dihydropyridines to be used as starting materials have not previously been disclosed, but can be obtained (according to German application No. P 2 658 183.9 corresponding to U.S. application Ser. No. 856,559 filed Dec. 1, 1977) by reacting β-ketocarboxylic acid esters of the formula

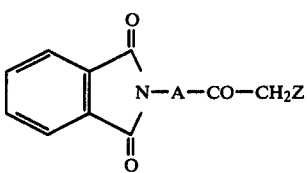

wherein A and Z have the same meaning as defined hereinbefore in formula (I) with enamines of the formula

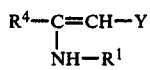

wherein $R^4$, $R^1$ and Y have the same meaning as described hereinbefore in formula (I) and aldehydes of the formula

wherein X has the same meaning as defined hereinbefore in formula (I).

2-Alkyleneaminodihydropyridines of the formula (I) in which $R^1$ is hydrogen, alkyl having from 1 to 4 carbon atoms, in particular methyl, alkoxyalkyl having a total of from 2 to 4 carbon atoms, or benzyl, A is an alkylene radical having from 1 to 4 carbon atoms, in particular methylene, ethylene, propylene, isopropylene, butylene or isobutylene, Y and Z are the same or different and each is a grouping $COOR^2$, wherein $R^2$ is alkyl having from 1 to 4 carbon atoms, in particular methyl, ethyl, propyl or isobutyl, or alkoxyalkyl having from 2 to 6 in particular with 2 to 4, carbon atoms, or an alkylaminoalkyl or alkylaminobenzyl radical, the alkyl moiety in each case having from 1 to 4 carbon atoms, $R^4$ is hydrogen, alkyl having from 1 to 4 carbon atoms, in particular methyl or ethyl, or a radical A—NH$_2$, wherein A has the same meaning as defined hereinbefore and X represents a phenyl radical optionally substituted by 1 or 2 identical or different substituents each of which is halogen, nitro, cyano, trifluoromethyl, amino, alkoxy having from 1 to 4 carbon atoms, in particular methoxy and ethoxy, or alkylmercapto having from 1 to 4 carbon atoms, in particular methylmercapto, or a naphthyl, pyridyl, thienyl, furyl or quinolyl ring, are particularly preferred.

Compounds according to the invention which may be mentioned are: 2-(β-aminoethyl)-6-ethyl-4-(2-methoxy-4-fluorophenyl)1,4-dihydropyridine-3,5-dicarboxylic acid propyl ester, 2,6-diaminomethyl-4-(3-nitrophenyl)-1,4-dihydropyridine-3-(carboxylic acid tert.-butyl ester)-5-carboxylic acid β-ethoxy ethyl ester, 2,6-(α-diaminopropyl)-4-β-pyridyl-1,4-dihydropyridine-3,5-dicarboxylic acid dibenzyl ester, 2-aminopropyl-6-propyl-4-(3-nitrophenyl)-1,4-dihydropyridine-3-(carboxylic acid butyl ester)-5-carboxylic acid isopropyl ester, 2-amino-methyl-6,1-methyl-4-(3-chlorophenyl)-1,4-dihydropyridine-3-(carboxylic acid ethyl ester)-5-carboxylic acid methoxypropyl ester, 2-aminomethyl-6-methyl-4-(2-nitro-4-chlorophenyl)-1,4-dihydropyridine-3-(carboxylic acid methyl ester)-5-acetyl and 2,6-diaminomethyl-4-(2-nitrophenyl)-1,4-dihydropyridine-3,5-dicarboxylic acid diethyl ester.

Unless expressly defined otherwise, in the present application the expression optionally substituted alkyl represents straight-chain or branched alkyl having preferably from 1 to 6, most preferably 1 to 4, carbon atoms. Examples which may be mentioned are optionally substituted methyl, ethyl, n-propyl, iso-propyl, n-butyl, iso-butyl and tert.-butyl.

Optionally substituted alkenyl is straight-chain or branched alkenyl having preferably from 2 to 6, most preferably from 2 to 4, carbon atoms. Examples which may be mentioned are optionally substituted ethenyl, propen-1-yl, propen-2-yl and buten-3-yl.

Optionally substituted alkinyl is straight-chain or branched alkinyl having preferably from 2 to 6, most preferably from 2 to 4, carbon atoms. Examples which may be mentioned are optionally substituted ethinyl, propin-1-yl, propin-2-yl and butin-3-yl.

Optionally substituted phenyl or naphthyl may be mentioned as preferred examples of optionally substituted aryl.

Optionally substituted aralkyl is aralkyl having preferably 6 or 10, most preferably 6, carbon atoms in the aryl moiety and preferably from 1 to 4, most preferably 1 or 2, carbon atoms in the alkyl moiety, the aryl moiety and/or the alkyl moiety being optionally substituted. Examples which may be mentioned are optionally substituted benzyl and phenethyl.

Halogen is preferably fluorine, chlorine, bromine or iodine, most preferably fluorine or chlorine.

Alkylamino preferably represents monoalkylamino or dialkylamino having from 1 to 4, most preferably 1 or 2, carbon atoms in the alkyl part in each case. Examples which may be mentioned are monomethylamino, N,N-dimethylamino, methylethylamino, methyl-benzylamino and n-butylamino. The carbalkoxy radicals mentioned preferably contain from 2 to 4 most preferably 2 or 3, carbon atoms. Examples which may be mentioned are carbomethoxy and carboethoxy.

The alkoxyalkyl substituents mentioned preferably contain 1 or 2 carbon atoms in the alkyl moiety and from 1 to 3 carbon atoms in the alkoxy moiety. Examples which may be mentioned are methoxyethyl, ethoxymethyl and propoxyethyl.

The free 2-alkyleneaminodihydropyridines of the general formula (I) and their salts can be interconverted in any suitable manner; methods for such interconversion are known in the art. For example the base may be dissolved in ether and a suitable acid added to the resulting solution.

Examples which may be mentioned of inorganic and organic acids which form physiologically acceptable acid addition salts with the free dihydropyridines of the formula (I) are: hydrogen halide acids, such as hydrochloric acid hydrobromic acid, especially hydrochloric acid, phosphoric acids, sulphuric acid, nitric acid, monofunctional and bifunctional carboxylic acids and hydroxycarboxylic acids, such as acetic acid, maleic acid, succinic acid, fumaric acid, tartaric acid, citric acid, salicylic acid, sorbic acid, lactic acid and 1,5-naphthalenedicarboxylic acid, and naphthalenedisulphonic acid.

Diluents which can be used in the preparation are water and all the inert organic solvents. These include, preferably, alcohols, for example lower alkyl alcohols having preferably from 1 to 4 carbon atoms, such as ethanol, methanol and isopropanol, ethers, for example lower dialkyl ethers (having preferably from 3 to 5 carbon atoms), such as diethyl ether, or cyclic ethers, such as tetrahydrofurane and dioxane, lower aliphatic carboxylic acids (having preferably from 2 to 5 carbon atoms), such as acetic acid and propionic acid, lower dialkylformamides (having preferably 1 or 2 carbon atoms per alkyl group), such as dimethylformamide, lower alkyl nitriles (having preferably from 2 to 4 carbon atoms), such as acetonitrile, dimethylsulphoxide, liquid hetero-aromatic bases, such as pyridine, and mixtures of these solvents, including water, with one another.

The reaction temperatures can be varied within a relatively wide range. In general, the reaction is carried out at from about 20° to 150° C., preferably from about 50° to 100° C., most preferably at the boiling point of the solvent used.

The reaction can be carried out under ambient pressure, but also under elevated pressure. In general, the reaction is carried out under atmospheric pressure.

The compounds according to the invention have a broad and diverse spectrum of pharmacological action.

In particular, the compounds according to the invention have the following principal actions:

1. On parenteral, oral and perlingual administration the new compounds produce a distinct and long-lasting dilation of the coronary vessels.

This action on the coronary vessels is intensified by a simultaneous nitrite-like effect of reducing the load on the heart. They influence or modify the heart metabolism in the sense of an energy saving.
2. The new compounds lower the blood pressure of normotonic and hypertonic animals and can thus be used as antihypertensive agents.
3. The excitability of the stimulus formation and excitation conduction system within the heart is lowered, so that an antifibrillation action demonstrable at therapeutic doses results.
4. The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).
5. The compounds have strongly muscular-spasmolytic actions which manifest themselves on the smooth muscle of the stomach, the intestinal tract, the urogenital tract and the respiratory system.
6. The compounds influence the cholesterol level and lipid level of the blood.

The new compounds are accordingly suitable for the prevention, amelioration or cure of diseases for which, in particular, the effects indicated above are desired.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention, in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution, e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from about 30 mg to 2.5 g of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably orally or parenterally, especially perlingually or intravenously. Preferred pharmaceutical compositions and medicaments are therefore those adapted for oral or parenteral administration, such as tablets and pills or injection solutions and suspensions, especially ampoules thereof, respectively. Administration in the method of the invention is preferably orally or parenterally.

In general it has proved advantageous to administer orally amounts of from about 0.1 mg to 100 mg preferably from 1 to 30 mg, per kg of body weight per day or parenterally (intravenously) from about 0.1 mg to 50 mg, preferably about 0.1 mg to 5 mg, per kg of body weight, per day, optionally in the form of at least two individual administrations, in order to achieve effective results. Advantageously individual dose administration is in amounts of from about 0.005 mg to 50 mg, preferably from 0.5 mg to 20 mg per kg of body weight. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

PREPARATIVE EXAMPLES

EXAMPLE 1

2-Aminomethyl-6-methyl-4-(2'-chlorophenyl)-1,4-dihydropyridine-3,5-dicarboxylic acid diethyl ester.

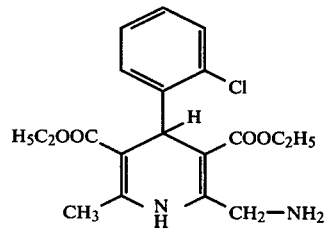

14 g of 2-phthalimidomethyl-6-methyl-4-(2-chlorophenyl)-1,4-dihydropyridine-3,5-dicarboxylic acid diethyl ester are heated to the boil in 150 ccs of ethanol, with the addition of 5 ccs of hydrazine hydrate, for 2–3 hours, the mixture is filtered hot and the filtrate is filtered again after cooling and concentrated in vacuo.

The residue is recrystallised from ether to give yellow crystals of melting point 134°–136° C., yield: 65%.

The following compounds were obtained in the same manner:

EXAMPLE 2

2-Aminomethyl-6-methyl-4-(3'-chlorophenyl)-1,4-dihydropyridine -3,5-dicarboxylic acid diethyl ester

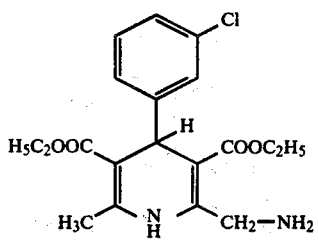

Melting point 140°–142° C. (ether), yield: 70%.

This compound is obtained by boiling 22 g of 2-phthalimidomethyl-6-methyl-4-(3'-chlorophenyl)-1,4-dihydropyridine-3,5-dicarboxylic acid diethyl ester and 11 g of hydrazine hydrate in 250 ccs of ethanol for 3 hours.

EXAMPLE 3

2-Aminomethyl-6-methyl-4-(3'-chlorophenyl)-1,4-dihydropyridine -3-(carboxylic acid ethyl ester)-5-carboxylic acid methyl ester

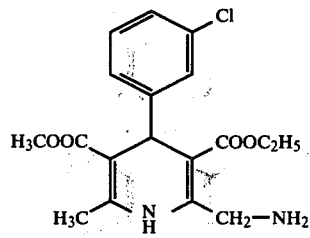

is obtained from 0.1 mol of 2-phthalimidomethyl-6-methyl-4-(3'-chlorophenyl)-1,4-dihydropyridine-3-(carboxylic acid ethyl ester)-5-carboxylic acid methyl ester and 22 ccs of hydrazine hydrate in 500 ccs of ethanol.

Light yellow crystals (ether) of melting point 128°–130° C.

Yield: 60%.

EXAMPLE 4

2-Aminomethyl-6-methyl-4-(2'-nitrophenyl)-1,4-dihydropyridine-3-(carboxylic acid ethyl ester)-5-carboxylic acid methyl ester

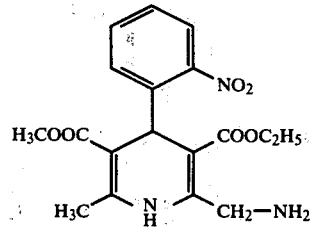

is obtained from 0.1 mol of 2-phthalimidomethyl-6-methyl-4-(2'-nitrophenyl)-1,4-dihydropyridine-3-(carboxylic acid ethyl ester)-5-carboxylic acid methyl ester and 22 ccs of hydrazine hydrate in 500 ccs of ethanol.

Light yellow crystals of heating point 134°–136° C.
Yield: 40%.

Example 5

2-Aminomethyl-6-methyl-4-(4'-methoxyphenyl)-1,4-dihydropyridine-3,5-dicarboxylic acid diethyl ester

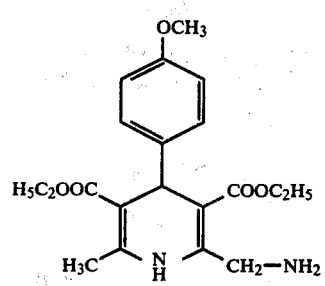

is obtained from 0.2 mol of 2-phthalimidomethyl-6-methyl-4-(2'-methoxyphenyl)-3,5-(dicarboxylic acid diethyl ester)-1,4-dihydropyridine and 22 ccs of hydrazine hydrate in 500 ccs of ethanol.

Yellow crystals (ether) of melting point 78°–80° C.
Yield: 65%.

EXAMPLE 6

2-Aminomethyl-6-methyl-4-(2'-trifluoromethylphenyl)-1,4-dihydropyridine-3,5-dicarboxylic acid diethyl ester

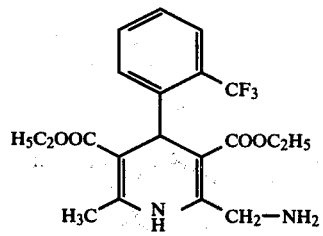

is obtained from 0.1 mol of 2-phthalimidomethyl-6-methyl-4-(2'-trifluoromethylphenyl)-1,4-dihydropyridine-3,5-dicarboxylic acid diethyl ester and 22 ccs of hydrazine hydrate in 500 ccs of ethanol.

Light yellow crystals of melting point 136°–138° C. (ether).

Yield: 50%.

EXAMPLE 7

2-Aminomethyl-6-methyl-4-(3'-nitrophenyl)-1,4-dihydropyridine -3-(carboxylic acid ethyl ester)-5-carboxylic acid methyl ester

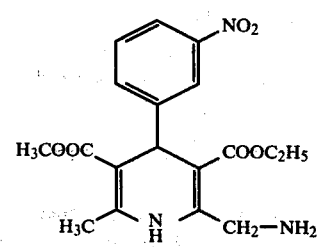

is obtained from 0.1 mol of 2-phthalimidomethyl-6-methyl-4-(3'-nitrophenyl)-1,4-dihydropyridine-3-(carboxylic acid ethyl ester)-5-carboxylic acid methyl ester and 20 ccs of hydrazine hydrate in 500 ccs of ethanol.

Light yellow crystals of melting point 137°–138° C. (ether).

Yield: 40%.

EXAMPLE 8

2-Aminomethyl-6-methyl-4-(α-pyridyl)-1,4-dihydropyridine-3,5-dicarboxylic acid diethyl ester

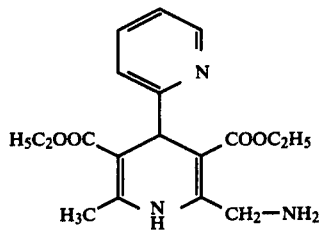

is obtained from 0.1 mol of 2-phthalimidomethyl-6-methyl-4-(α-pyridyl)-1,4-dihydropyridine-3,5-dicarboxylic acid diethyl ester and 20 ccs of hydrazine hydrate in 500 ccs of ethanol.

EXAMPLE 9

2-Aminomethyl-6-methyl-4-(β-pyridyl)-1,4-dihydropyridine-3,5-dicarboxylic acid diethyl ester

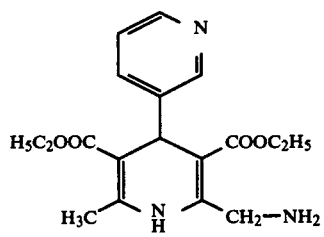

is obtained from 0.1 mol of 2-phthalimidomethyl-6-methyl-4-(β-pyridyl)-1,4-dihydropyridine-3,5-dicarboxylic acid diethyl ester and 20 ccs of hydrazine hydrate in 500 ccs of ethanol.

EXAMPLE 10

2-Aminomethyl-6-methyl-4-phenyl-1,4-dihydropyridine-3,5-dicarboxylic acid diethyl ester

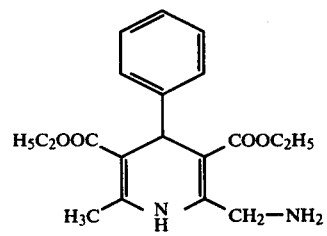

is obtained from 0.1 mol of 2-phthalimidomethyl-6-methyl-4-phenyl-1,4-dihydropyridine-3,5-dicarboxylic acid diethyl ester and 20 ccs of hydrazine hydrate in 500 ccs of ethanol.

EXAMPLE 11

2-Aminomethyl-6-methyl-4-(2'-methoxyphenyl)-1,4-dihydropyridine-3-(carboxylic acid aethyl ester)-5-carboxylic acid methyl ester

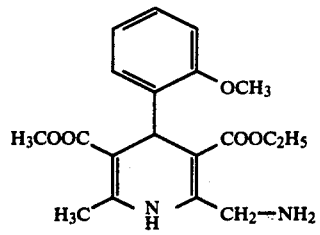

is obtained from 2-phthalimidomethyl-6-methyl-4-(2'-methoxyphenyl)-1,4-dihydropyridine-3-(carboxylic acid ethyl ester)-5-carboxylic acid methyl ester and 20 ccs of hydrazine hydrate in 500 ccs of ethanol.

EXAMPLE 12

2-Aminomethyl-6-methyl-4-(2'-methylmercaptophenyl)-1,4-dihydropyridine-3,5-dicarboxylic acid diethyl ester

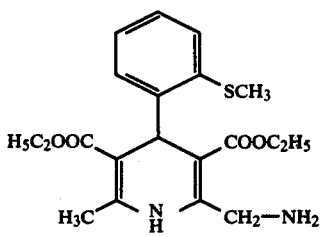

is obtained from 2-phthalimidomethyl-6-methyl-4-(2'-methylmercaptophenyl)-1,4-dihydropyridine-3,5-dicarboxylic acid diethyl ester and 20 ccs of hydrazine hydrate in 500 ccs of ethanol.

EXAMPLE 13

2-Aminomethyl-6-methyl-4-(2'-nitro-3'-methoxyphenyl)-1,4-dihydropyridine-3-(carboxylic acid ethyl ester)-5-carboxylic acid methyl ester

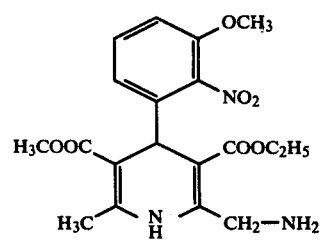

is obtained from 2-phthalimidomethyl-6-methyl-4-(2'-nitro-3'-methoxyphenyl)-1,4-dihydropyridine-3-(carboxylic acid ethyl ester)-5-carboxylic acid methyl ester and 20 ccs of hydrazine hydrate in 500 ccs of ethanol.

EXAMPLE 14

2-Aminomethyl-6-methyl-4-(4'-nitrophenyl)-1,4-dihydropyridine -3,5-dicarboxylic acid diethyl ester

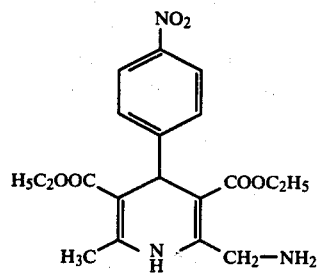

is obtained from 2-phthalimidomethyl-6-methyl-4-(4'-nitrophenyl)-1,4-dihydropyridine-3,5-dicarboxylic acid diethyl ester and 20 ccs of hydrazine hydrate in 500 ccs of ethanol.

EXAMPLE 15

2-Aminomethyl-6-methyl-4-(γ-pyridyl)-1,4-dihydropyridine-3,5-dicarboxylic acid diethyl ester

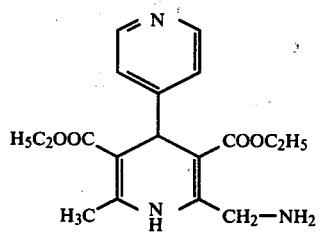

is obtained from 2-phthalimidomethyl-6-methyl-4-(γ-pyridyl-1,4-dihydropyridine-3,5-dicarboxylic acid diethyl ester and 20 ccs of hydrazine hydrate in 500 ccs of ethanol.

EXAMPLE 16

2-Aminomethyl-6-methyl-4-(4'-fluorophenyl)-1,4-dihydropyridine-3,5-dicarboxylic acid diethyl ester

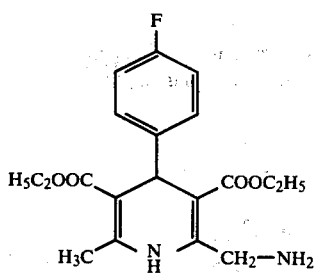

is obtained from 2-phthalimidomethyl-6-methyl-1,4-dihydropyridine-3,5-dicarboxylic acid diethyl ester and 20 ccs of hydrazine hydrate in 500 ccs of ethanol.
Yield: 75%.

EXAMPLE 17

2-Aminomethyl-6-methyl-4-(3'-cyanophenyl)-1,4-dihydropyridine-3,5-dicarboxylic acid diethyl ester

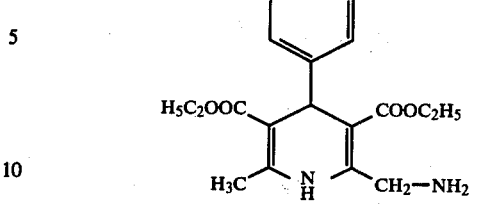

is obtained from 2-phthalimidomethyl-6-methyl-4-(3'-cyanophenyl)-1,4-dihydropyridine-3,5-dicarboxylic acid diethyl ester and 20 ccs of hydrazine hydrate in 500 ccs of ethanol.
Yellowish crystals of melting point 110°–112° C.
Yield: 50%.

EXAMPLE 18

2,6-(Diaminomethyl)-4-(2'-chlorophenyl)-1,4-dihydropyridine-3,5-dicarboxylic acid diethyl ester

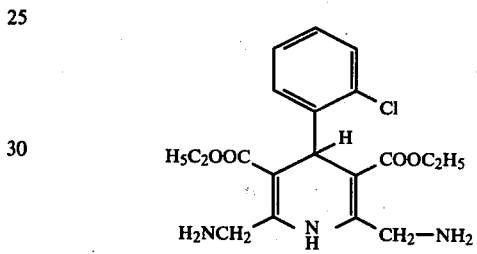

20 g of 2,6-(diphthalimidomethyl)-4-(2'-chlorophenyl)-1,4-dihydropyridine-3,5-dicarboxylic acid diethyl ester are heated to the boil in 600 ccs of ethanol, with the addition of 12 ccs of hydrazine hydrate, for 3 hours, the mixture is filtered hot and the filtrate is then filtered cold and evaporated in vacuo.
Light yellow crystals (ether) of melting point 115° C.
Yield: 40%.

EXAMPLE 19

2-Aminomethyl-6-methyl-4-(3'-fluorophenyl)-1,4-dihydropyridine-3-(carboxylic acid ethyl ester)-5-carboxylic acid β-methoxyethyl ester

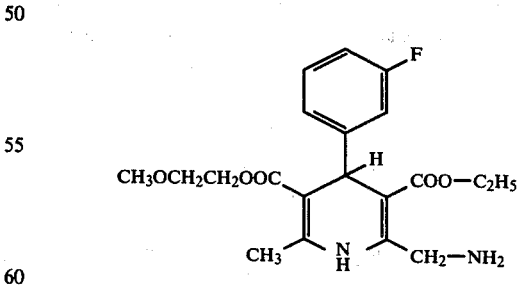

is obtained from 0.1 mole of 2-phthalimidomethyl-6-methyl-4-(3'-fluorophenyl)-1,4-dihydropyridine-3-(carboxylic acid ethyl ester)-5-carboxylic acid β-methoxyethyl ester and 20 ccs of hydrazine hydrate in 1,000 ccs of ethanol.
Light yellow crystals of melting point 78°–80° C.
Yield: 75%.

EXAMPLE 20

2-Aminomethyl-6-methyl-4-(2'-chlorophenyl)-1,4-dihydropyridine-3-(carboxylic acid ethyl ester)-5-carboxylic acid allyl ester

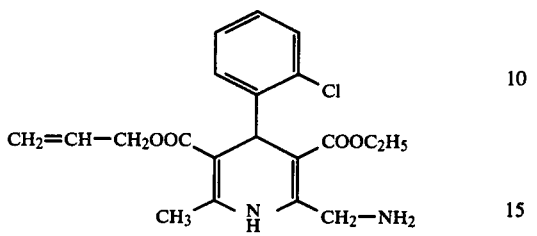

is obtained from 0.1 mol of phthalimidomethyl-6-methyl-4-(2'-chlorophenyl)-1,4-dihydropyridine-3-(carboxylic acid ethyl ester)-5-carboxylic acid allyl ester and 20 ccs of hydrazine hydrate in 1,000 ccs of ethanol.

Light yellow crystals of melting point 120° C.
Yield: 60%.

EXAMPLE 21

2-Aminomethyl-6-methyl-4-(2'-chlorophenyl)-1,4-dihydropyridine-3-(carboxylic acid ethyl ester)-5-carboxylic acid propargyl ester

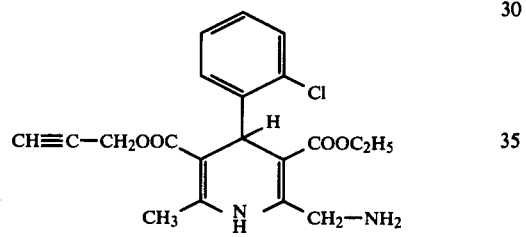

is obtained from 0.1 mol of 2-phthalimidomethyl-6-methyl-4-(2'-chlorophenyl)-1,4-dihydropyridine-3-(carboxylic acid ethyl ester)-5-carboxylic acid propargyl ester and 20 ccs of hydrazine hydrate in 1,000 ccs of ethanol.

Light yellow crystals of melting point 115° C.
Yield: 60%.

EXAMPLE 22

2-Aminomethyl-6-methyl-4-phenyl-1,4-dihydropyridine-3-(carboxylic acid ethyl ester)-5-carboxylic acid isopropyl ester

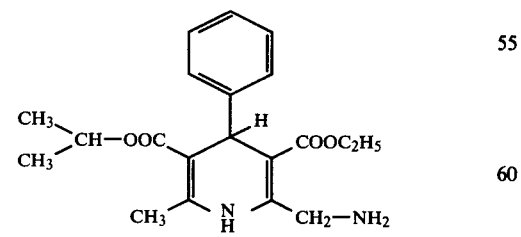

is obtained from 0.1 mol of 2-phthalimidomethyl-6-methyl-4-phenyl-3-(carboxylic acid ethyl ester)-5-carboxylic acid isopropyl ester and 20 ccs of hydrazine in 1,000 ccs of ethanol.

Light yellow crystals of melting point 98° C.

Yield: 50%.

EXAMPLE 23

2-Aminomethyl-6-methyl-4-(2'-ethoxyphenyl)-3-carboxylic acid ethyl ester)-5-carboxylic acid methyl ester

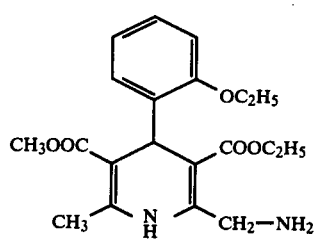

is obtained from 0.1 mol of 2-phthalimidomethyl-6-methyl-4-(2'-ethoxyphenyl)-1,4-dihydropyridine-3-(carboxylic acid ethyl ester)-5-carboxylic acid methyl ester and 20 ccs of hydrazine hydrate in 1,000 ccs of ethanol.

Light yellow crystals of melting point 151° C.
Yield: 70%.

EXAMPLE 24

2-Aminomethyl-6-methyl-4-(3'-chlorophenyl)-1,4-dihydropyridine-3-(carboxylic acid ethyl ester)-5-carboxylic acid benzyl ester

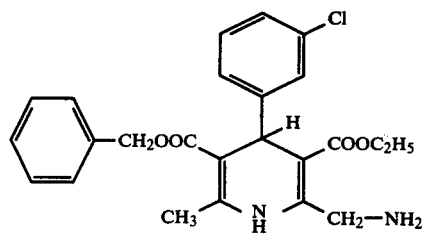

is obtained from 0.1 mol of 2-phthalimido-6-methyl-4-(3'-chlorophenyl)-1,4-dihydropyridine-3-(carboxylic acid ethyl ester)-5-carboxylic acid benzyl ester and 20 ccs of hydrazine hydrate in 1,000 ccs of ethanol.

Light yellow crystals of melting point 73°–75° C.
Yield 90%.

What is claimed is:

1. A 2-Alkleneaminodihydropyridine of the general formula or pharmaceutically acceptable salts thereof

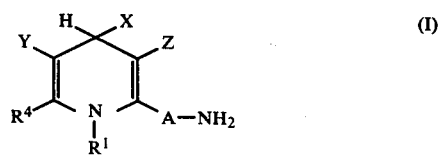

in which $R^1$ is hydrogen, alkyl having from 1 to 4 carbon atoms, alkoxyalkyl having a total of from 2 to 4 carbon atoms or aralkyl having 6 to 10 carbon atoms in the aryl moiety and 1 to 4 carbon atoms in the alkyl moiety A is a straight-chain or branched divalent alkylene radical, having 1 to 4 carbon atoms, Y and Z are the same or different and each is
 (a) a grouping $COOR^2$,
wherein $R^2$ is alkyl, alkenyl, alkinyl, alkoxyalkyl, hydroxyalkyl, aminoalkyl, alkylaminoalkyl, alkylaminoaralkyl or aralkyl, wherein each of the alkyl groups and moieties have 1 to 4 carbon atoms, each of said alkenyl and alkinyl groups have 2 to 6 carbon atoms and each of said aralkyl groups and moieties have 6 to 10 carbon atoms;

$R^4$ is hydrogen, or alkyl having 1 to 4 carbon atoms, optionally substituted by alkoxy having 1 to 4 carbon atoms, or is a radical A—NH$_2$, wherein A has the same meaning as defined hereinbefore, and X is phenyl or naphthyl optionally substituted by from one to two identical or different substituents each of which is halogen, nitro, cyano, trifluoromethyl, amino, alkoxy having from 1 to 4 carbon atoms, or alkylmercapto having from 1 to 4 carbon atoms.

2. A compound according to claim 1 in which $R^1$ is hydrogen, alkyl having from 1 to 4 carbon atoms, alkoxyalkyl having a total of from 2 to 4 carbon atoms or benzyl, A is an alkylene radical having from 1 to 4 carbon atoms, Y and Z are the same or different and each is a grouping COOR$^2$, wherein $R^2$ is alkyl having from 1 to 4 carbon atoms, or alkoxyalkyl having from 2 to 6 carbon atoms, or an alkylaminoalkyl or alkylaminobenzyl radical, the alkyl moiety in each case having from 1 to 4 carbon atoms, $R^4$ is hydrogen, alkyl having from 1 to 4 carbon atoms, or a radical A—NH$_2$, wherein A has the same meaning as defined hereinbefore, and X is phenyl or naphthyl optionally substituted by 1 or 2 identical or different substituents each of which is halogen, nitro, cyano, trifluoromethyl, amino, alkoxy having from 1 to 4 carbon atoms, or alkylmercapto having from 1 to 4 carbon atoms.

3. A compound according to claim 2 wherein $R^1$ is hydrogen, A is methylene, Y and Z are each COOR$^2$ wherein $R^2$ is alkyl having from 1 to 4 carbon atoms, $R^4$ is alkyl having from 1 to 4 carbon atoms or a radical A—NH$_2$, wherein A has the same meaning as defined hereinbefore and X is phenyl which is unsubstituted or substituted by 1 or 2 identical or different substituents each of which is halogen, nitro, cyano, trifluoromethyl, amino, alkoxy having from 1 to 4 carbon atoms, or alkylmercapto having from 1 to 4 carbon atoms.

4. A compound according to claim 3 wherein X is phenyl substituted by 1 substituent.

5. A compound according to claim 1 which is 2-aminomethyl-6-methyl-4-(2'-chlorophenyl)-1,4-dihydropyridine-3,5-dicarboxylic acid diethyl ester.

6. A compound according to claim 1 which is 2-aminomethyl-6-methyl-4-(4'-fluorophenyl)-1,4-dihydropyridine-3,5-dicarboxylic acid diethyl ester.

7. A pharmaceutical vasodilator and antihypertensive composition comprising as an active ingredient an effective amount of a compound according to claim 1 in admixture with a solid or liquefied gaseous diluent or in admixture with a liquid diluent other than a solvent of a molecular weight less than 200 except in the presence of a surface-active agent.

8. A pharmaceutical vasodilator and antihypertensive composition comprising as an active ingredient an effective amount of a compound according to claim 1 in the form of a sterile or isotonic aqueous solution.

9. A composition according to claim 7 wherein the active ingredient is 2-aminomethyl-6-methyl-4-(2'-chlorophenyl)-1,4-dihydropyridine-3,5-dicarboxylic acid diethyl ester.

10. A pharmaceutical vasodilator and antihypertensive composition comprising as an active ingredient an effective amount of a compound according to claim 6 in admixture with a solid or liquefied gaseous diluent or in admixture with a liquid diluent other than a solvent of a molecular weight less than 200 except in the presence of a surface-active agent.

11. A composition according to claim 7 comprising from 0.5 to 95% by weight of the said active ingredient.

12. A medicament in dosage unit form comprising an effective amount for vasodilator or antihypertensive effect of a compound of claim 1 together with an inert pharmaceutical carrier.

13. A medicament in the form of a tablet, pill, dragee, capsule, ampoule, or suppository comprising an effective amount for vasodilator or antihypertensive effect of a compound according to claim 1.

14. A method of combating a circulatory disorder in warm-blooded animals in need of such treatment by providing vasodilator or antihypertensive effect which comprises administering orally or parenterally to the said animals an effective amount of an active compound according to claim 1 either alone or in admixture with a diluent or in the form of a medicament.

15. A method according to claim 14 in which the active compound is administered orally in an amount of from 0.1 to 100 mg or parenterally in an amount of from 0.01 to 50 mg, per kg body weight per day.

16. A method according to claim 15 in which the animals are ruminants.

17. A method according to claim 16 in which the active compound is administered orally.

* * * * *

UNITED STATES PATENT AND TRADEMARK OFFICE
CERTIFICATE OF CORRECTION

PATENT NO. : 4,177,278
DATED : December 4, 1979
INVENTOR(S) : Friedrich Bossert, et al.

It is certified that error appears in the above-identified patent and that said Letters Patent are hereby corrected as shown below:

Column 15, line 66, after "hydrazine" insert

--hydrate--.

Signed and Sealed this

Twenty-fifth Day of March 1980

[SEAL]

Attest:

SIDNEY A. DIAMOND

Attesting Officer    Commissioner of Patents and Trademarks